US012797511B2

(12) United States Patent
Zeng et al.

(10) Patent No.: US 12,797,511 B2
(45) Date of Patent: Nov. 17, 2026

(54) CARDIOVASCULAR IMPLANT BASED ON IN-SITU REGULATION OF IMMUNE RESPONSE AND METHOD FOR MAKING THE SAME

(71) Applicant: Army Medical University, Chongqing (CN)

(72) Inventors: Wen Zeng, Chongqing (CN); Yanzhao Li, Chongqing (CN); Yanhong Wang, Chongqing (CN); Fangchao Xue, Chongqing (CN)

(73) Assignee: Army Medical University, Chongqing (CN)

( * ) Notice: Subject to any disclaimer, the term of this patent is extended or adjusted under 35 U.S.C. 154(b) by 165 days.

(21) Appl. No.: 18/079,064

(22) Filed: Dec. 12, 2022

(65) Prior Publication Data

US 2023/0211046 A1 Jul. 6, 2023

(30) Foreign Application Priority Data

Dec. 29, 2021 (CN) ........................ 202111646804.5

(51) Int. Cl.

| | |
|---|---|
| ***A61L 27/22*** | (2006.01) |
| ***A61K 47/68*** | (2017.01) |
| ***A61K 47/69*** | (2017.01) |
| ***A61L 27/36*** | (2006.01) |
| ***A61L 27/50*** | (2006.01) |

(52) U.S. Cl.

CPC ........ *A61L 27/227* (2013.01); *A61K 47/6849* (2017.08); *A61K 47/6931* (2017.08); *A61L 27/3625* (2013.01); *A61L 27/507* (2013.01); *A61L 2300/254* (2013.01); *A61L 2300/256* (2013.01); *A61L 2300/258* (2013.01); *A61L 2300/602* (2013.01); *A61L 2430/20* (2013.01)

(58) Field of Classification Search

CPC ............ A61K 47/6849; A61K 47/6931; A61K 47/6957; A61L 2300/256; A61L 27/3625; A61L 27/507; A61L 2400/12; A61L 2300/258; A61L 2300/602; A61L 27/227; C12N 2310/20

See application file for complete search history.

(56) References Cited

PUBLICATIONS

Li et al, CRISPR/Cas9 therapeutics progress and prospects, Signal Transduction and Targeted Therapy, vol. 8, Issue 36, pp. 1-23, published Jan. 16, 2023 (Year: 2023).*

Wang et al, Programming of Regulatory T Cells In Situ for Nerve Regeneration and Long-Term Patency of Vascular Grafts. Research. vol. 2022, Issue 9826426, pp. 1-17, Jul. 25, 2022 (Year: 2022).*

* cited by examiner

*Primary Examiner* — Jennifer Dunston
*Assistant Examiner* — Lexus M Tatge
(74) *Attorney, Agent, or Firm* — Gearhart Law LLC

(57) ABSTRACT

Provided is a cardiovascular implant based on in-situ regulation of immune response and a method for making the same, belonging to the technical field of biomedicine. The cardiovascular implant includes a cardiovascular implant body and H4000-CD25/dcas9 sustained-release nanoparticles modified on the cardiovascular implant body; the H4000-CD25/dcas9 sustained-release nanoparticles include an H4000 plasmid nanocarrier, an anti-CD25 antibody, and a dcas9 plasmid sequence; a method for preparing the cardiovascular implant includes: constructing a cardiovascular implant body, preparing an H4000-CD25 nanotransfection vector, preparing H4000-CD25/dcas9 sustained-release nanoparticles, and conjugating the H4000-CD25/dcas9 sustained-release nanoparticles on the cardiovascular implant body. The cardiovascular implant modified with the H4000-CD25/dcas9 sustained-release nanoparticles may induce nerve fiber ingrowth into engineered blood vessels; with the regulation ability of Treg cells on immune response, antithrombotic function of the cardiovascular implant is improved and in-situ regeneration of the cardiovascular implant is promoted.

6 Claims, 12 Drawing Sheets

Specification includes a Sequence Listing.

SEQUENCE LISTING

Sequence total quantity: 4
SEQ ID NO: 1 moltype = DNA length = 4104
FEATURE Location/Qualifiers
source 1..4104
mol_type = other DNA
note = DNA sequence of the dcas9 plasmid
organism = synthetic construct
SEQUENCE: 1

```
atggacaaga agtactccat tggcctcgcc atcggaacaa atagcgtggg ctgggctgtc  60
atcacagatg agtacaaggt gcctagcaag aaatttaagg tgctgggaaa tacagacaga  120
catagcatca agaagaacct cattggcgct ctcctgtttg actccggcga aacagccgaa  180
gctaccagac tcaagagaac cgctaggaga aggtacacca gaaggaaaaa caggatttgc  240
tacctgcagg aaatttttc caacgagatg gccaaggtgg acgattcctt cttccatagg  300
ctggaagaga gcttcctcgt ggaggaagac aagaaacacg agaggcatcc tatttttggc  360
aatattgtgg atgaggtcgc ctaccatgag aagtatccca caatctatca tctgagaaaa  420
aaactggtgg atagcaccga caaggccgat ctcaggctca tttatctcgc tctggctcac  480
atgatcaagt ttaggggcca cttcctgatc gaaggcgacc tgaatcccga caactccgac  540
gtggacaaac tgttcatcca gctcgtccag acctacaatc aactcttcga ggagaacccc  600
atcaatgctt ccggcgtgga tgccaaggcc atcctgagcg ctaggctctc caagtccagg  660
aggctggaaa atctgatcgc ccaactccct ggagagaaga agaacggcct gtttggcaat  720
ctgattgccc tgagcctcgg actcaccccc aacttcaaga gcaacttcga tctcgccgaa  780
gacgccaaac tccaactgag caaggatacc tacgacgacg atctcgataa tctcctcgcc  840
cagatcggcg atcaatatgc cgacctcttt ctggccgcca aaaacctgag cgacgctatt  900
ctgctcagcg acattctcag ggtgaataca gaaatcacaa aagcccccct gtccgccagc  960
atgatcaaaa ggtacgatga acaccatcag gacctcaccc tgctgaaggc tctggtcagg  1020
cagcaactcc ccgaaaagta caaggagatt ttctttgatc agtccaagaa tggatatgct  1080
ggctatattg atggaggcgc ctcccaggag gaattttata aattcatcaa gcccattctc  1140
gaaaagatgg acggaaccga agagctgctg gtcaaactca atagggagga tctgctgagg  1200
aagcaaagga ccttcgacaa tggcagcatc ccccaccaga tccacctcgg cgaactccac  1260
gctatcctca ggaggcagga agacttctac cctttcctga aggataacag ggagaaaatc  1320
gagaaaatcc tgaccttcag aatcccctac tacgtcggac ctctcgccag gggcaattcc  1380
agattcgcct ggatgacaag gaagagcgag gaaacaatca caccatggaa cttcgaagaa  1440
gtggtcgata agggcgccag cgcccagagc ttcattgaaa ggatgaccaa ctttgataag  1500
aacctgccca atgagaaggt gctgcctaag cactccctgc tgtatgagta tttcaccgtg  1560
tataatgagc tgaccaaggt caagtacgtc accgagggaa tgagaaagcc tgcttttctc  1620
tccggcgagc agaaaaaagc catcgtggac ctgctgttca agaccaacag gaaggtgacc  1680
gtcaagcaac tcaaggagga ctactttaag aagattgagt gctttgatag cgtggaaatt  1740
agcggagtcg aggacaggtt caatgcctcc ctcggaacat atcacgacct gctgaaaatc  1800
atcaaagaca aagattttct ggataacgag gagaatgaag acattctgga ggacattgtc  1860
ctcaccctga ccctgtttga ggacagagag atgattgaag agaggctgaa aacctatgcc  1920
cacctgttcg acgacaaggt gatgaagcag ctcaaaagaa ggagatatac cggctggggc  1980
agactgtcca ggaagctgat caacggcatt agggacaagc agagcggcaa gaccattctc  2040
gactttctca agtccgacgg attcgccaac agaaacttta tgcaactgat ccacgatgac  2100
agcctcacct ttaaggaaga tattcagaag gctcaggtca gcggccaagg cgattccctc  2160
catgagcaca tcgctaatct ggctggctcc cctgctatca aaaagggcat cctccagaca  2220
gtcaaagtcg tcgatgagct ggtcaaggtg atgggcaggc ataaacccga gaacattgtg  2280
attgagatgg ctagggagaa ccagaccacc cagaaaggcc agaaaaacag cagagaaaga  2340
atgaagagga tcgaggaggg catcaaagaa ctgggcagcc aaatcctcaa ggagcacccc  2400
gtcgaaaata cacaactcca gaacgaaaaa ctctacctct actatctgca gaacggcaga  2460
gacatgtacg tggaccagga actggacatc aacaggctct ccgattacga tgtggacgcc  2520
atcgtccctc agtcctttct gaaagatgat agcatcgaca acaaggtgct gaccaggtcc  2580
gacaagaata ggggcaagag cgataatgtg ccctccgagg aggtcgtcaa aaaaatgaaa  2640
aactactgga gacaactcct caacgctaag ctcatcaccc aaagaaagtt cgacaatctg  2700
accaaagccg agaggggcgg cctctccgaa ctggacaagg ccggcttcat caaaaggcaa  2760
ttggtggaaa ccaggcagat tacaaagcat gtcgctcaaa ttctcgatag caggatgaat  2820
accaaatatg acgagaacga caagctgatc agagaggtca aggtcatcac actcaagtcc  2880
aagctcgtga gcgacttcag aaaagatttc caattttata aagtcaggga gatcaacaat  2940
taccaccacg ctcacgacgc ttatctcaac gctgtcgtgg gaaccgccct gatcaaaaaa  3000
taccccaagc tggaaagcga gttcgtgtat ggcgattata aagtgtacga cgtgaggaag  3060
atgatcgcta aaagcgagca ggaaatcggc aaggctacag ccaagtactt tttctactcc  3120
aacattatga acttcttcaa gaccgagatt accctcgcca acggcgaaat taggaagagg  3180
cccctgattg aaacaaatgg agaaacaggc gaaatcgtct gggacaaggg cagggacttc  3240
gccacagtca gaaaagtgct gtccatgcct caagtcaaca tcgtcaaaaa gaccgaggtg  3300
cagaccggcg gctttagcaa agaaagcatc ctgcccaaga gaaactccga caagctcatc  3360
gctaggaaga aggactggga ccctaagaaa tacggaggat ttgactcccc taccgtcgcc  3420
tattccgtcc tcgtcgtcgc taaggtggag aagggcaaga gcaagaagct caagagcgtc  3480
aaggagctgc tgggaatcac catcatggag aggagctcct tcgaaaaaaa ccctattgat  3540
ttcctggagg ccaagggcta caaggaggtc aagaaggacc tcatcatcaa gctgcccaaa  3600
tacagcctct tcgaactgga aaatggcagg aagagaatgc tcgctagcgc cggcgagctc  3660
cagaaaggaa atgagctggc tctgcccagc aagtacgtca acttcctcta tctcgccagc  3720
cactatgaaa agctcaaggg cagccccgaa gacaatgagc agaagcagct cttcgtcgag  3780
cagcacaagc actacctcga tgaaatcatc gagcaaatca gcgagttttc caaaagggtg  3840
attctcgccg acgctaacct cgataaggtc ctctccgctt acaacaagca tagagacaag  3900
cccatcagag aacaggccga gaacatcatc cacctgttta cactcacaaa cctcggagcc  3960
cctgccgctt ttaaatactt cgatacaacc attgatagga agaggtacac ctccaccaag  4020
gaggtgctgg atgctaccct gattcatcaa tccatcacag gactctacga aacaaggatt  4080
```

-continued

```
gacctgtccc aactgggagg cgac                                         4104

SEQ ID NO: 2            moltype = DNA  length = 21
FEATURE                 Location/Qualifiers
source                  1..21
                        mol_type = other DNA
                        note = sgRNA1
                        organism = synthetic construct
SEQUENCE: 2
ccgcccggag gagccccgcc g                                            21

SEQ ID NO: 3            moltype = DNA  length = 23
FEATURE                 Location/Qualifiers
source                  1..23
                        mol_type = other DNA
                        note = sgRNA2
                        organism = synthetic construct
SEQUENCE: 3
agtcacgtcc gccccctcgg cgg                                          23

SEQ ID NO: 4            moltype = DNA  length = 23
FEATURE                 Location/Qualifiers
source                  1..23
                        mol_type = other DNA
                        note = sgRNA3
                        organism = synthetic construct
SEQUENCE: 4
gccccgccgc gcctccgcga ggg                                          23
```

CARDIOVASCULAR IMPLANT BASED ON IN-SITU REGULATION OF IMMUNE RESPONSE AND METHOD FOR MAKING THE SAME

CROSS REFERENCE TO RELATED APPLICATION

This patent application claims the benefit and priority of Chinese Patent Application No. 202111646804.5 filed with the China National Intellectual Property Administration on Dec. 29, 2021, the disclosure of which is incorporated by reference herein in its entirety as part of the present application.

REFERENCE TO SEQUENCE LISTING

A computer readable XML file having the file name "40O4513.XML", that was created on Dec. 18, 2025, with a file size of about 9,398 bytes, contains the sequence listing for this application, has been filed with this application, and is hereby incorporated by reference in its entirety.

TECHNICAL FIELD

The present disclosure relates to the technical field of biomedicine, in particular to a cardiovascular implant based on in-situ regulation of immune response and a method for making the same.

BACKGROUND

Cardiovascular disease is the No. 1 disease threatening human health. Worldwide, 7.3 million people die of ischemic heart disease every year, which ranks first among all diseases. Therefore, there is an increasing demand for cardiovascular implants. Among them, biological blood vessel prostheses are the development direction of vascular implants for coronary artery bypass grafting, hemodialysis and peripheral vascular occlusion treatment. In addition, the construction of complex tissues and organs like liver, kidneys, lungs, and islets of Langerhans requires vascularization, resulting in a further increase in the demand for biological blood vessel prostheses. A human being is an entirety, and the functioning of a certain organ in one system often requires the interaction and regulation of other systems. Especially, the transplanted tissues and organs need to be integrated into the recipient as soon as possible to rebuild normal connections with the recipient's various systems.

However, current research on organ transplantation mainly focuses on allograft rejection and functional reconstruction, with little attention paid to neural network reconstruction. Nerves, especially sympathetic nerves, play a crucial role in the maintenance of immune homeostasis. Sympathetic nerves innervate vasoconstriction and glandular secretion. Catecholamines (CAs), ATP, and adenosine secreted by sympathetic nerves have been shown to inhibit interleukin (IL-12), tumor necrosis factor (TNF)-α, and interferon (IFN)-γ, but promote the production of IL-10, which protects tissues and organs from damage caused by excessive inflammatory response. Therefore, neural network reconstruction may be a new target for maintaining the immune privilege and long-term functioning of renal allografts.

Inflammation is a "double-edged sword" for tissue regeneration. Low-intensity inflammation can promote the mobilization and proliferation of stem cells, while persistent inflammation will damage stem cell function; how to realize in-situ regulation of immune response to promote inflammation resolution remains to be an important problem in the art.

To solve the above problems, a cardiovascular implant based on in-situ regulation of immune response and a method for making the same are provided in light of the prior art.

SUMMARY

An objective of the present disclosure is to provide a cardiovascular implant based on in-situ regulation of immune response and a method for making the same. In this method, a cardiovascular implant modified with H4000-CD25/dcas9 sustained-release nanoparticles is constructed utilizing the influence and effect of different severity of inflammation on the regeneration of the cardiovascular implant, which can induce nerve fiber ingrowth into engineered blood vessels; also, with the regulation ability of Treg cells on immune response, antithrombotic function of the cardiovascular implant is improved and in-situ regeneration of the cardiovascular implant is promoted; in addition, when the cardiovascular implant prepared by the present method is used for vascular grafting, sustained-release nanoparticles may regulate the immune response in situ, accelerate revascularization, effectively overcome the thrombosis, and promote long-term vascular patency.

The foregoing technical objective of the present disclosure is achieved through the following technical solutions:

A cardiovascular implant based on in-situ regulation of immune response is provided, including a cardiovascular implant body and H4000-CD25/dcas9 sustained-release nanoparticles modified on the cardiovascular implant body. The H4000-CD25/dcas9 sustained-release nanoparticles include an H4000 plasmid nanocarrier (Engreen), an anti-CD25 antibody, and a dcas9 plasmid sequence. The H4000 plasmid nanocarrier and the anti-CD25 antibody are covalently linked, and the dcas9 plasmid sequence is used to enhance the expression of demethylase TET2.

In some embodiments, the dcas9 plasmid sequence is pZdonor_U6-sgRNA-EF1α-dSpCas9-NLS-VP64-2A-EGFP-2A-Puro.

In some embodiments, the cardiovascular implant is tubular, 1-4 mm in diameter, and 0.5-20 cm in length.

The present disclosure further provides a method for preparing a cardiovascular implant based on in-situ regulation of immune response, including the following steps:

step 1, constructing a cardiovascular implant body;

step 2, preparing an H4000-CD25 nanotransfection vector;

step 3, preparing H4000-CD25/dcas9 sustained-release nanoparticles by the H4000-CD25 nanotransfection vector and a Crispr/dcas9 system plasmid; and step 4, conjugating the H4000-CD25/dcas9 sustained-release nanoparticles on the cardiovascular implant body: co-incubating the cardiovascular implant body with the H4000-CD25/dcas9 sustained-release nanoparticles and collagen to obtain the cardiovascular implant.

In some embodiments, a method for constructing the cardiovascular implant body in step 1 includes: removing cells, then nucleic acids and fats from isolated blood vessels to obtain a blood vessel matrix material; and covering collagen on a surface of the blood vessel matrix material to obtain the cardiovascular implant body.

In some embodiments, the H4000-CD25/dcas9 sustained-release nanoparticles in step 3 are prepared by encapsulating the Crispr/dcas9 system plasmid on the H4000-CD25 nanotransfection vector, where the Crispr/dcas9 system plasmid is incubated with the H4000-CD25 nanotransfection vector at 0.4 μg of plasmid/μL of transfection vector.

In some embodiments, a method for conjugating the H4000-CD25/dcas9 sustained-release nanoparticles on the cardiovascular implant body in step 4 includes: conducting a first incubation of the cardiovascular implant body with the H4000-CD25/dcas9 sustained-release nanoparticles for 10 min, conducting a second incubation of the cardiovascular implant body with the collagen for 10 min; and repeating the incubations twice to obtain a self-assembled cardiovascular implant modified with the H4000-CD25/dcas9 sustained-release nanoparticles.

The technological principle is as follows: The cardiovascular implant body will cause an inflammatory response after implantation in the body due to the certain immunogenicity thereof, especially at the anastomotic stoma between the blood vessel and the cardiovascular implant. Moreover, acute inflammation in blood vessels further propagates chronic inflammation by promoting the infiltration of leukocytes and plasma proteins. Both acute and chronic inflammatory responses are important predisposing causes of vascular implant thrombosis and difficult intimal regeneration or abnormal hyperplasia.

First of all, in order to avoid the strong immune rejection of the body, cells in isolated blood vessels are first removed, and then nucleic acids and fats in the isolated blood vessels are removed to obtain a blood vessel matrix material; the cardiovascular implant of the present scheme is made into a small-diameter cardiovascular implant (namely, small-diameter tissue-engineered blood vessel, also known as small-diameter TEBV, with a diameter of 1-4 mm), which can solve the clinical problem of high failure rate after small-diameter vascular graft. Generally, small-diameter TEBVs are 0.5-20 cm in length, which can meet the needs of clinical applications like vascular graft.

In the present technical scheme, transfection reagent H4000 is a cationic polymer carrying substantial amino groups, which are conjugated with the carboxyl groups on the anti-CD25PE antibody to form an H4000-CD25PE specific nanocarrier, and then forms an H4000-CD25/dcas9 sustained-release nanocarrier with a dcas9 plasmid to be modified on the cardiovascular implant body; after vascular graft, due to the inflammatory response, Treg cells infiltrate outside the blood vessels, so that the encapsulated nanomaterial was transfected and infiltrated into extravascular Treg cells. The in vivo targeted transfection effect of Treg cells is improved by conjugating an anti-CD25 antibody onto the nanotransfection material, so as to achieve in-situ regulation of immune response, accelerate vascular and nerve regeneration, effectively overcome the thrombosis, and promote long-term vascular patency.

After the Crispr/dcas9 system is transfected into Treg cells, the expression of a TET2 gene promoter is enhanced, and the expression of TET2 protein is upregulated, thereby regulating the secretion of Treg cell-related cytokines, and further promoting the nerve reconstruction of Crispr/dcas9-modified engineered blood vessels. In this way, faster implantation of grafted blood vessel prostheses by the nerves is promoted to integrate the prostheses into the homeostasis in the body, preventing the blood vessel prostheses from calcification and blockage.

To sum up, the embodiments of the present disclosure has the following beneficial effects:

1. The influence and effect of different severity of inflammation on the regeneration of the cardiovascular implant is utilized in the present disclosure to construct a cardiovascular implant modified with H4000-CD25/dcas9 sustained-release nanoparticles, which can induce nerve fiber ingrowth into engineered blood vessels.

2. The cardiovascular implant modified with H4000-CD25/dcas9 sustained-release nano-system is prepared in the present disclosure. When the cardiovascular implant is used for vascular graft, the sustained-release nanoparticles may regulate the immune response in situ, accelerate revascularization, effectively overcome the thrombosis, and promote long-term vascular patency.

3. The cardiovascular implant constructed by this method may efficiently recognize the aggregated Treg cells, activate and enhance inflammatory inhibition thereof, and realize in-situ regulation of attached macrophages, thereby promoting inflammatory outcome and creating an excellent local microenvironment to accelerate vascular and nerve regeneration; the antithrombotic function of the cardiovascular implant is improved and in-situ regeneration of the cardiovascular implant is accelerated.

4. The collagen used in this method is of high safety and biocompatibility. Given the characteristics of high mechanical strength, strong pressure bearing ability and excellent biocompatibility of collagen nanoparticles, the transfected nanoparticles are encapsulated in the collagen and cross-linked on the surface of the cardiovascular implant body by layer-by-layer self-assembly, achieving sustained release of H4000-CD25/dcas9 nanoparticles and prolonging the expiration date of patency of the cardiovascular implant.

DETAILED DESCRIPTION OF THE EMBODIMENTS

Figure 1:
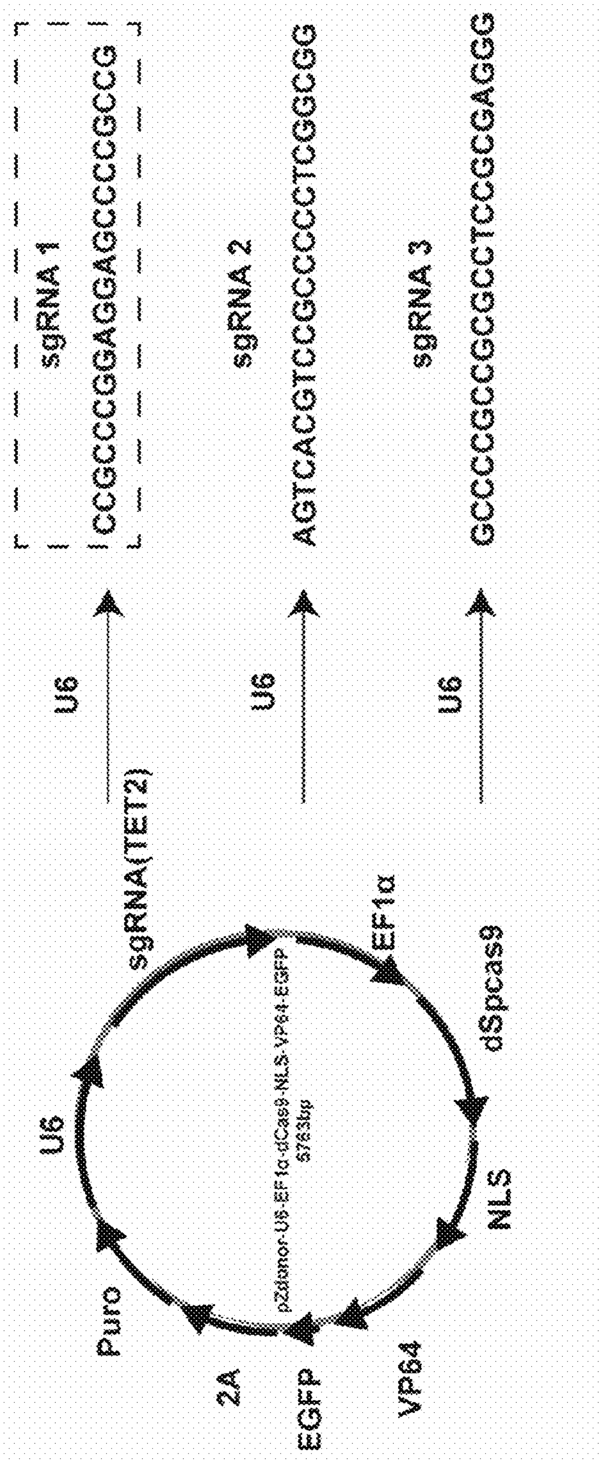
FIG. 1 is a schematic diagram that illustrates a sequence of Crispr/dcas9 system plasmid including sgRNA1 (SEQ ID NO: 2), sgRNA2 (SEQ ID NO: 3), and sgRNA3 (SEQ ID NO: 4) in Example 1 of the present disclosure.
Figure 2:
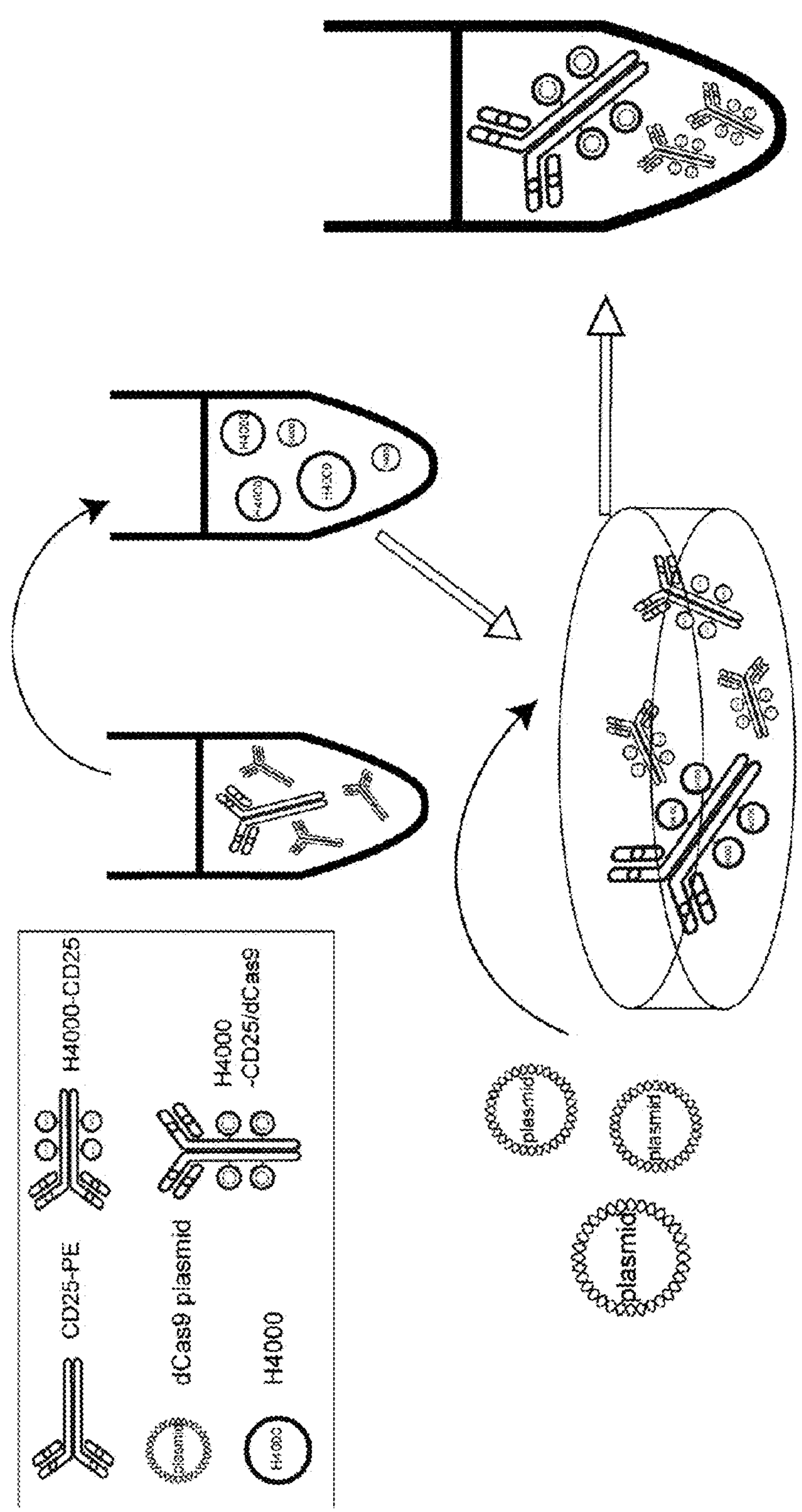
FIG. 2 is a schematic diagram that illustrates the spatial distribution of H4000-CD25 and the preparation process of an H4000-CD25/dcas9 transfection plasmid in Example 1 of the present disclosure.
Figure 3:
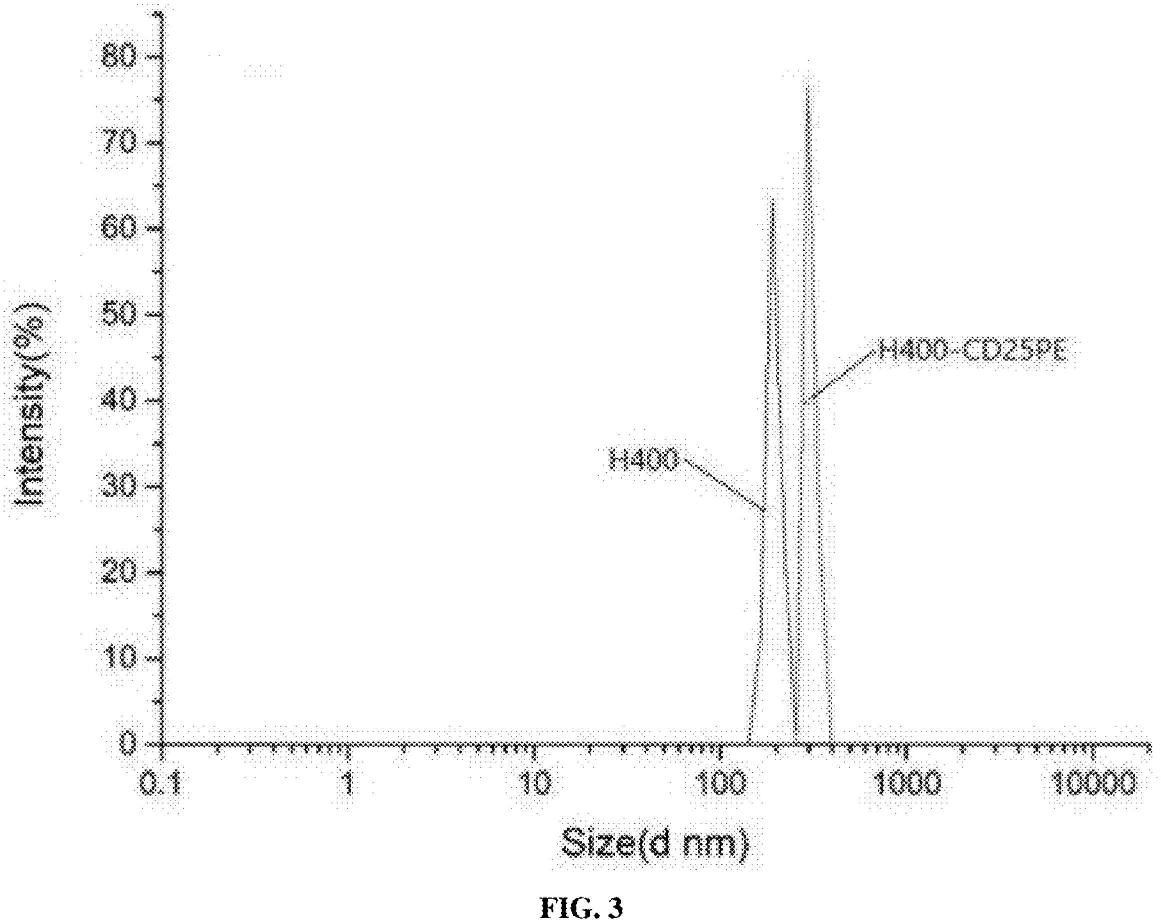
FIG. 3 illustrates hydrodynamic sizes of H4000 and H4000-CD25PE.

The present disclosure will be further described in detail below with reference to accompanying drawings and an example:

Example: A method for preparing a cardiovascular implant based on in-situ regulation of immune response was provided, as shown in FIGS. 1, 2, and 3, including the following steps:

(1) constructing a cardiovascular implant body:

a) under sterile conditions, the common carotid artery was extracted from a SD rat weighing 250-300 g, the blood was washed away with normal saline; the outer connective tissue of the common carotid artery was separated and removed, and cut into small blood vessels with a length of 0.5-1 cm (generally, tissue engineered blood vessels with a length of 0.5-20 cm can meet the needs of clinical applications, such as vascular graft, and the transplantation recipients of the cardiovascular implant are rats, so a small blood vessel with a length of 0.5-1 cm is preferred).

Trypsin was diluted with M199 medium to a concentration of 0.05%, the blood vessels were digested and treated at 37° C. for 30 min to remove cells, and nucleic acid and fat were removed with RNase, DNase, and lipase to obtain a blood vessel matrix material with only collagen and elastic fibers present. Herein, the blood vessel matrix material was 1-4 mm in diameter, so as to ensure the preparation of a small-diameter cardiovascular implant (TEBV) with a diameter that met the requirements.

b) the blood vessel matrix material was incubated with a 4 mg/mL collagen solution for 24 h to obtain a cardiovascular implant body.

(2) preparation of H4000-CD25 nanotransfection vector: Transfection reagent H4000 was conjugated with anti-CD25-PE antibody (12-0390-82, eBioscience) to form H4000-CD25 transfection nanoparticles. The specific steps were as follows:

a) 20 μL of H4000 was diluted to 1 mL to measure the hydrodynamic size of H4000.

b) 20 μL of H4000 was diluted to 1 mL to test the zeta potentials of H4000 at pH 7.4 and at pH 4.7, respectively; the results showed the zeta potential of H4000 was 3.5 mV both at pH 7.4 and pH 4.7, without obvious potential change.

c) 40 μL (namely 8 μg) of 0.2 mg/mL CD25-PE was pipetted and 15 μL of 10×MES (4-morpholineethanesulfonic acid, pH 5.5) buffer was added.

d) 100 μL of H4000 was pipetted, mixed well and incubated for 1 h on a shaker at 25° C. in the dark; 8 μL (namely 8 μg) of EDC (N1-((ethylimino)methylene)-N3, N3-dimethylpropane-1,3-diamine, 1 mg/mL, diluted with MES) was added, and incubated overnight on the shaker in the dark.

e) a resulting mixture was ultrafiltered with pure water at 100 KDa three times, and the volume was made up to 100 μL.

The hydrodynamics and zeta potential of the product were measured to determine the conjugation effect. The volume was 20 μL, and the hydrodynamic size of H4000 was increased from 193 nm to 306 nm, indicating that the conjugation was successful. The particle size of nanoparticles was observed under scanning electron microscope.

(3) the Crispr/dcas9 system plasmid was encapsulated onto the H4000-CD25 nanotransfection vector to form H4000-CD25/dcas9 sustained-release nanoparticles. The specific steps were as follows:

a) 0.8 μg of dcas9 plasmid was diluted with 25 μL of serum-free diluent and mixed well to prepare a dcas9 diluent.

The serum-free diluent was recommended to be reduced serum medium (OPTI-MEM®), serum-free DMEM or 1640.

b) 2 μL of Entranster™-H4000/H4000-CD25PE was diluted with 25 μL of serum-free diluent and mixed well to prepare an Entranster™-H4000/H4000-CD25PE diluent, which was let stand for 5 min at room temperature.

c) the Entranster™-H4000 diluent was added separately to the dcas9 diluent, mixed well, and let stand for 15 min at room temperature (or shaken on a shaker or pipetted with a sampler more than 10 times), and the preparation of H4000-CD25/dcas9 sustained-release nanoparticles was completed. The incubation ratio of Crispr/dcas9 system plasmid to H4000-CD25 nanotransfection vector was 0.4 μg of plasmid/μL of transfection vector.

(4) H4000-CD25/dcas9 sustained-release nanoparticles were conjugated onto the cardiovascular implant body, which was specifically as follows:

a) H4000-CD25/dcas9 sustained-release nanoparticles were added to a culture vessel containing cells and complete medium, and mixed well gently.

b) the cardiovascular implant body was soaked in the working solution containing H4000-CD25PE/dcas9 sustained-release nanoparticles for 10 min and then in phosphate-buffered saline (PBS) for 2 min; the cardiovascular implant body was soaked in soluble collagen PBS (1 g/L) for 10 min and then in PBS for 2 min, and the incubation and elution steps were repeated twice to obtain a self-assembled cardiovascular implant modified with H4000-CD25/dcas9 sustained-release nanoparticles.

In the present disclosure, a series of tests for quality control and characterization was further carried out, and the results were as follows:

(1) Observation of morphology and various indicators

Figure 6:
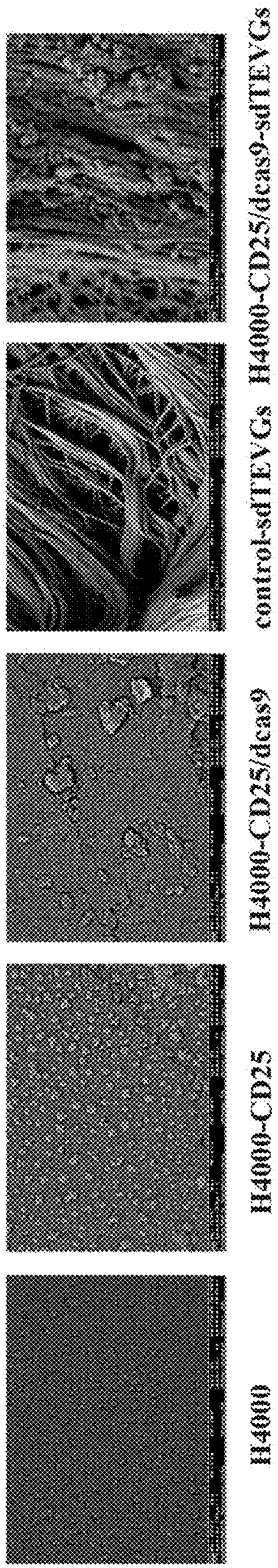
FIG. 6 illustrates the size and surface morphology of a nanocomposite in Example 1 of the present disclosure (inside and outside of biological tissue, observed under scanning electron microscope)

The cardiovascular implant was taken out, and the morphology and various indicators were observed, as shown in FIG. 6. A control group was set up in this experiment, which was the cardiovascular implant body.

Measurement of nanoparticle size under scanning electron microscope: Five groups were subjected to scanning electron microscopy, including three blood vessel-free groups (H4000 group, H4000-CD25 group and H4000-CD25/dcas9 group) and two blood vessel incubation groups (pure acellular blood vessel group and H4000-CD25/dcas9 blood vessel incubation group). For the blood vessel-free groups, one droplet was dropped onto a mica sheet to dry. The blood vessel incubation groups needed to be incubated with glutaraldehyde overnight before scanning, and dehydrated with alcohol and tert-butanol gradiently. All groups were mounted on the mechanical stage for gold plating and photographing.

Figure 4:
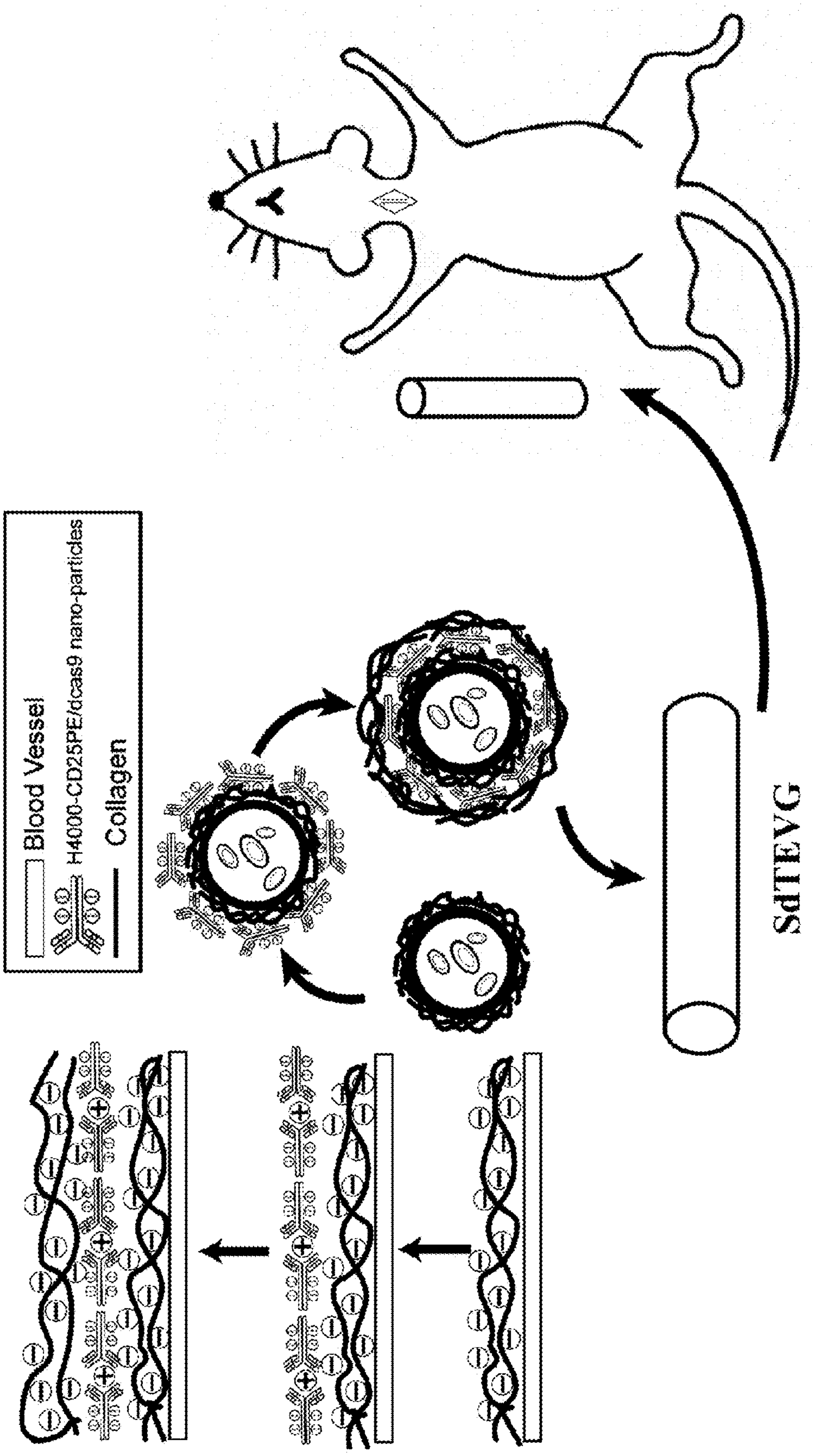
FIG. 4 is a schematic diagram that illustrates the preparation and transplantation of an H4000-CD25/dcas9 vascular sustained-release system.
Figure 5:
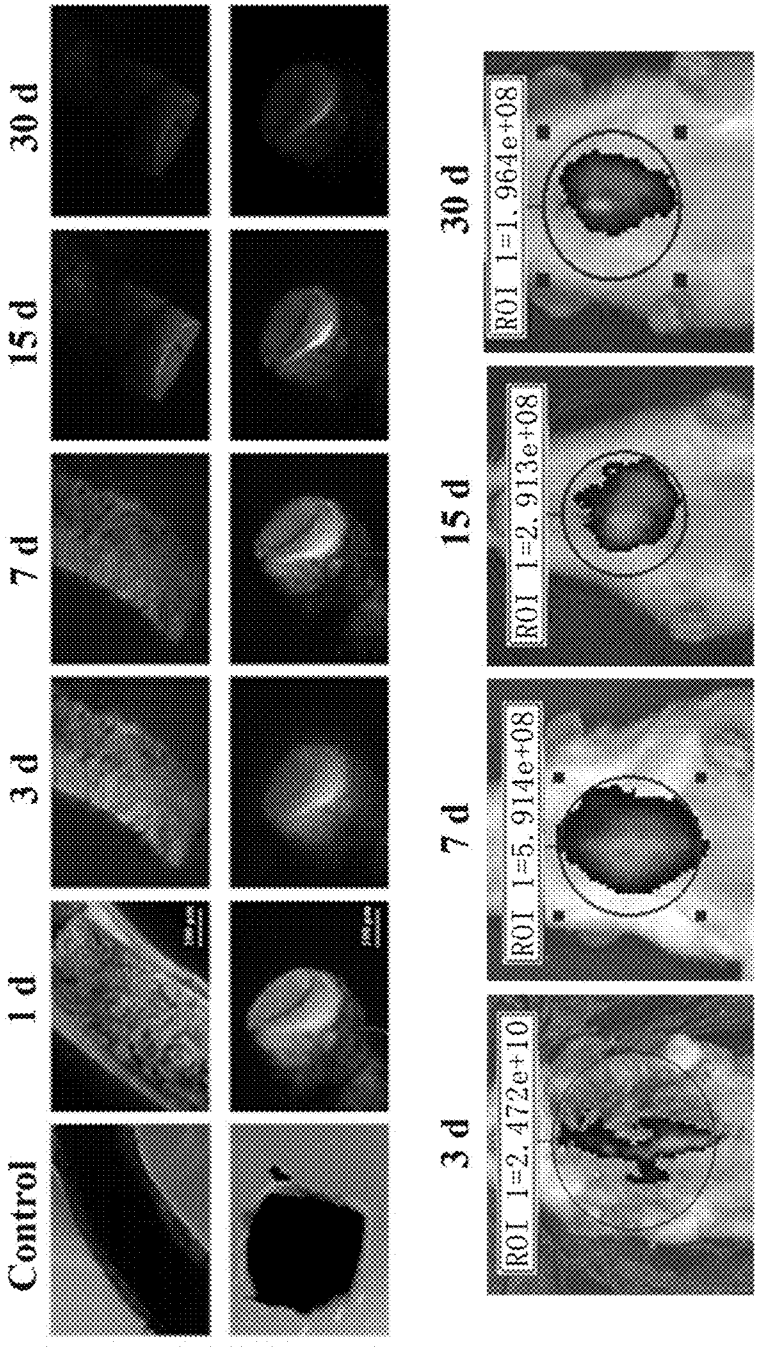
FIG. 5 is a diagram that illustrates the maintenance effect of H4000-Cy3/dcas9 and in vivo fluorescence on detection of vascular sustained-release fluorescence in vitro and in vivo.

(1) Detection of the sustained-release effect:

a) Residue detection of cardiovascular implant nanoparticles is as shown in FIGS. 4 and 5.

Preparation of H4000-Cy3 Nanoparticles:

Step 1, reaction of H4000 with Cy3: 10 μL of activated Cy3 (5 mg/mL), 200 μL of H4000, and 200 μL of $NaHCO_3$ (0.1 M, pH 7.8) were mixed well, and reacted overnight at 4° C. in the dark.

Step 2, dialysis (the specification of the dialysis bag was 3500 Da): the dialysis bag was boiled with 50% ethanol for half an hour to activate, sealed with clips at both ends, put in a deionized water bath and stirred, with the water changed every 2 h, and dialyzed overnight after the last time of changing for collection.

Figure 11:
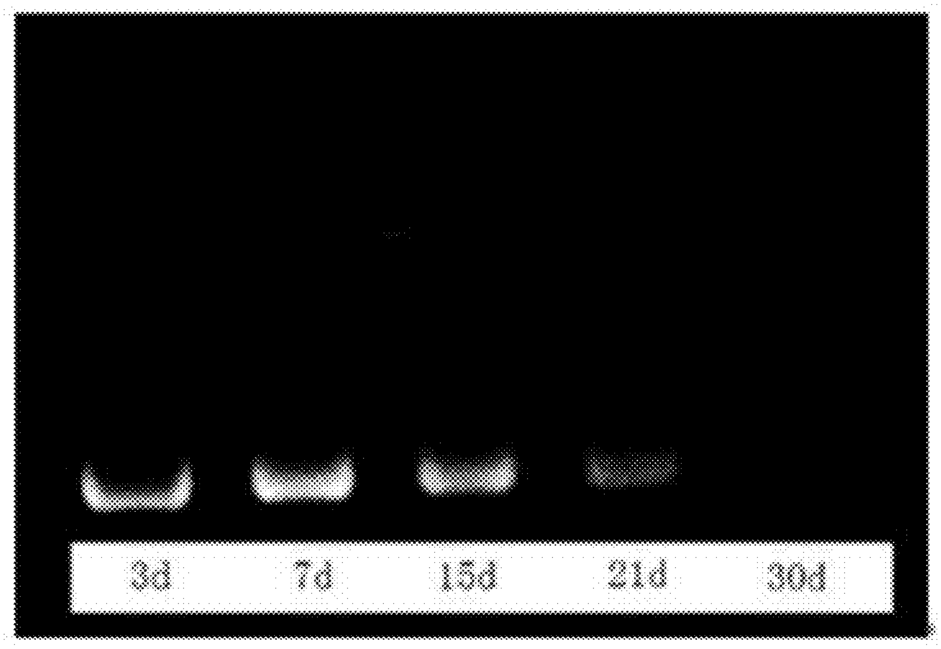
FIG. 11 illustrates the observation of sustained release of a plasmid by plasmid PCR amplification.

Step 3, the foregoing H4000-Cy3 cardiovascular implant was placed in 1.5% agarose gel in normal saline, photographs were taken at 1/3/7/15/30 days to compare the residual fluorescence of Cy3, respectively, and the residual DIR fluorescence in vivo was observed with an in vivo imaging system at 1/3/7/15/30 days after transplantation, respectively.

b) Cardiovascular implant plasmid release assay: As shown in FIG. 11, the foregoing H4000-CD25PE/dcas9 engineered blood vessel was placed in a 1.5% agarose in normal saline. Plasmids were amplified by PCR at 1/3/7/15/30 days to observe the sustained release of the plasmids, respectively.

Figure 7:
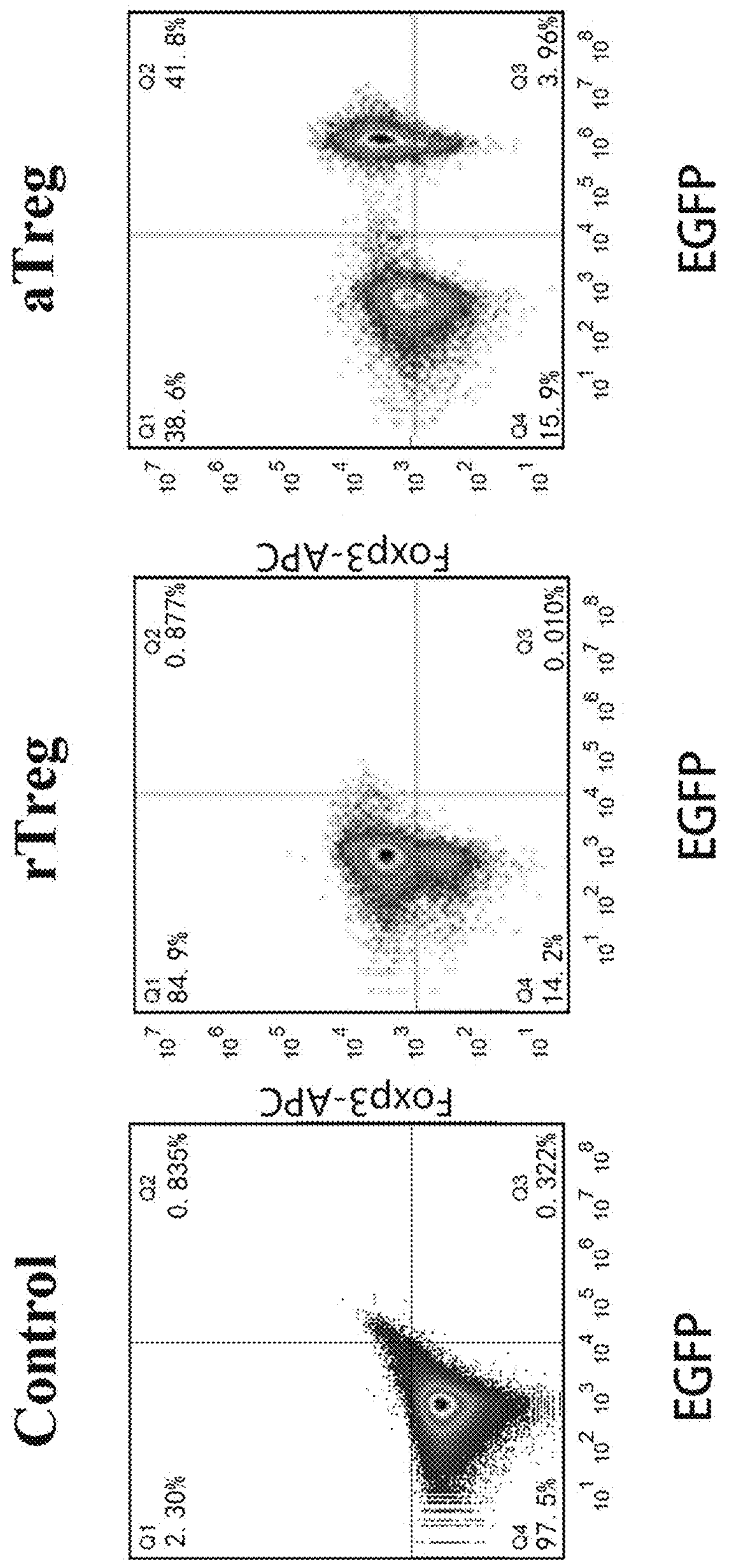
FIG. 7 shows flow cytometry scatter plots of the transfection efficiency of Treg cells by H4000-CD25/dcas9 system (including control group and positive results)
Figure 8:
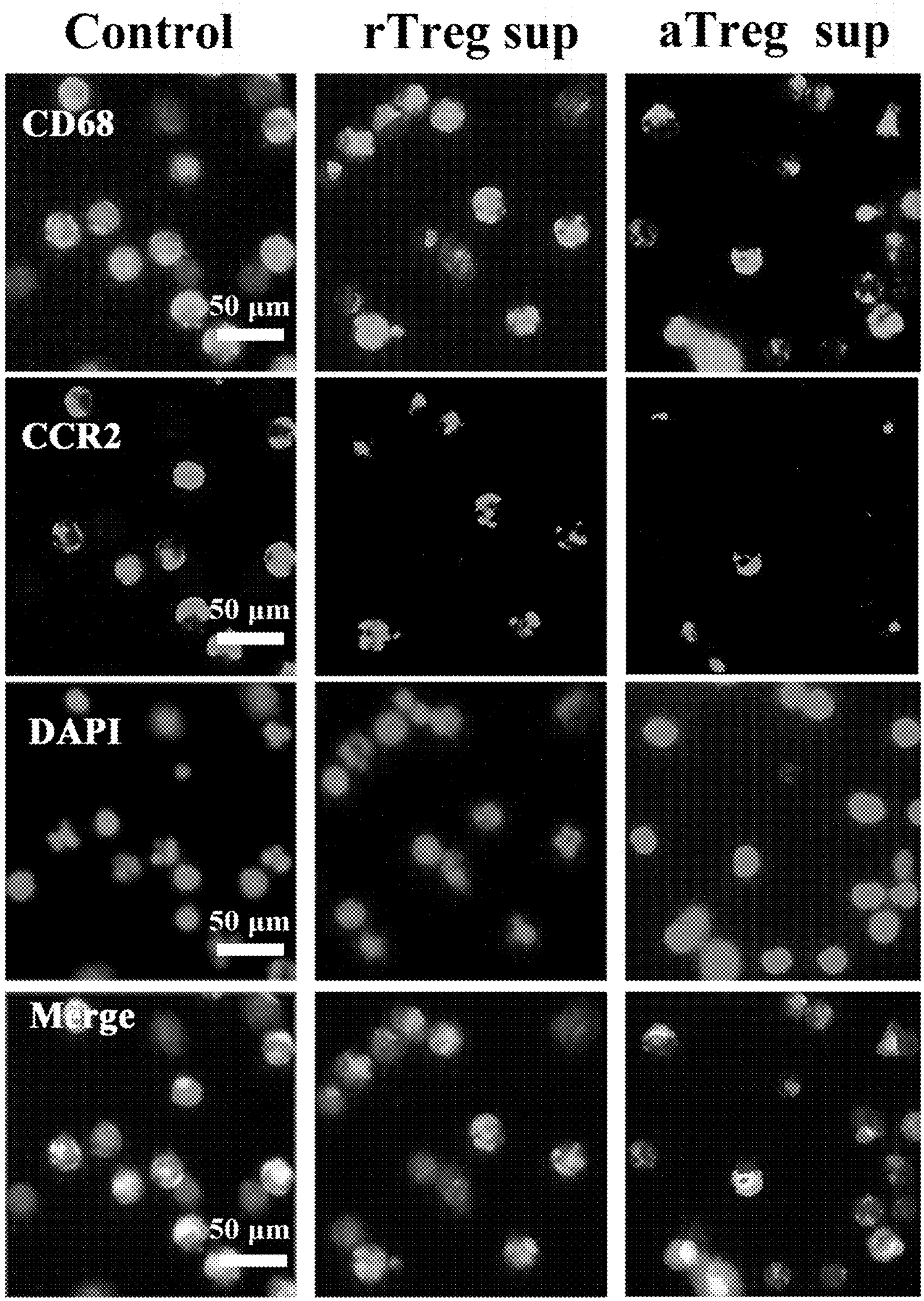
FIG. 8 illustrates the effect of the expression of inflammatory factors in macrophages after transfection according to the present disclosure (observed under fluorescence microscope)

(2) Detection of the transfection efficiency and the effect on the release of inflammatory cytokines: As shown in FIGS. 7 and 8, at 24-48 h after transfection of Treg cells in vitro, incubation with rabbit GFP (bs-0844r, Bioss) and mouse FOXP3 primary antibodies (ab22510, abcam), as well as rabbit 488 and mouse 568 secondary antibodies (Thermo Fisher), was carried out, and the transfection efficiency was detected by flow cytometry (C6, BD). The expression changes of IL10, TGF and IL35 were detected by an ELISA kit (X-Y Biotechnology Co., Ltd.). Supernatants were collected from Treg cells in the H4000-CD25PE and H4000-CD25 PE/dcas9 groups two days after transfection, and added to the above macrophage medium at a ratio of 1:1. The culture was continued for two days. The supernatants were incubated with mouse CD68 (TA318150, ORIGENE) and rabbit CCR2 (GB11326, Servicebio) primary antibodies and with mouse 488 and rabbit 568 secondary antibodies, and the fluorescence was photographed.

Figure 9:
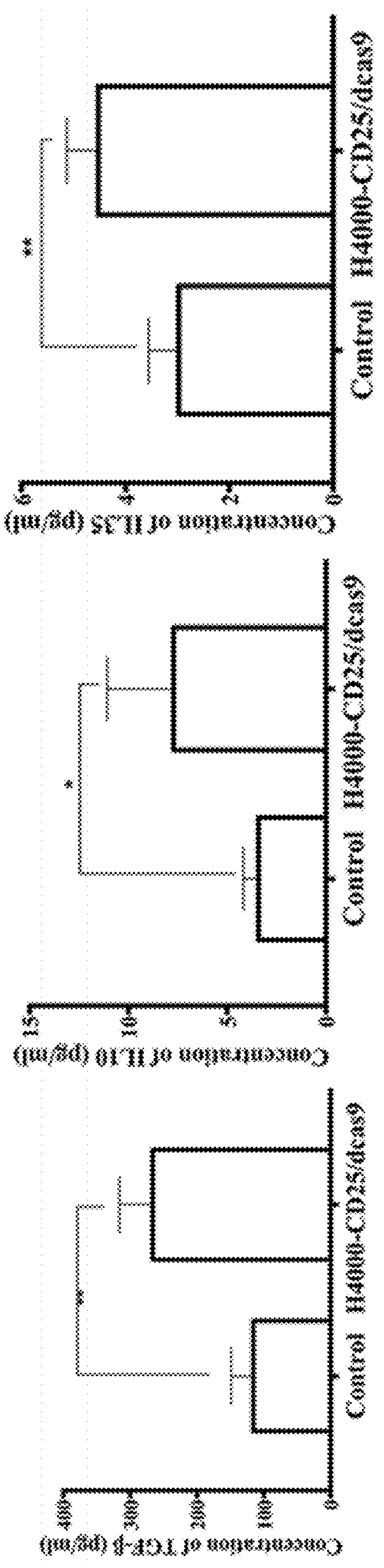
FIG. 9 illustrates the effect of cardiovascular implant on secretion of Treg anti-inflammatory factors (detected by ELISA)

(3) In vivo regulation of inflammatory response by the system: As shown in FIG. 9, at 24-48 h after transfection of Treg cells in vitro, incubation with rabbit GFP (bs-0844r, Bioss) and mouse FOXP3 primary antibodies (ab22510, abcam), and then rabbit 488 and mouse 568 secondary antibodies (Thermo Fisher), was performed, and the transfection efficiency was detected by flow cytometry (C6, BD). The expression changes of IL10, TGF and IL35 were detected by an ELISA kit (X-Y Biotechnology Co., Ltd.). The steps were as follows.

a) At 3/7/15/30 days, the foregoing transplanted acellular cardiovascular implant bodies and normal non-transplanted blood vessels were taken. After the clots of the blood vessels were rinsed with normal saline within 2 min, the blood vessels were transferred to 4% formalin for incubation for 3 h and then to 30% sucrose overnight; frozen sections were made and incubated with cd3 and foxp3 (abcam) primary antibodies, as well as cd68 and CCR2 (abcam) primary antibodies, respectively; incubation with mouse 488 and rabbit 568 secondary antibodies and DAPI was performed, and photographs were taken by confocal microscopy for in vivo detection of changes in immune cells of untransfected blood vessel grafts over time.

b) At 3/7/15 days, the transplanted engineered blood vessels from the above three groups (H4000-CD25PE, H4000/dcas9, and H4000-CD25PE/dcas9) were taken. After the clots of the blood vessels were rinsed with normal saline within 2 min, the blood vessels were transferred to 4% formalin to incubate for 3 h and then to 30% sucrose overnight; frozen sections were made and incubated with GFP (Servicebio) and foxp3 (abcam) primary antibodies, as well as cd68 (ORIGENE) and CCR2 (abcam) primary antibodies, respectively; incubation with mouse 488 and rabbit 568 secondary antibodies as well as DAPI was performed, and photographs were taken by confocal microscopy for in vivo detection of changes in immune cells of transfected blood vessel grafts over time.

Figure 10:
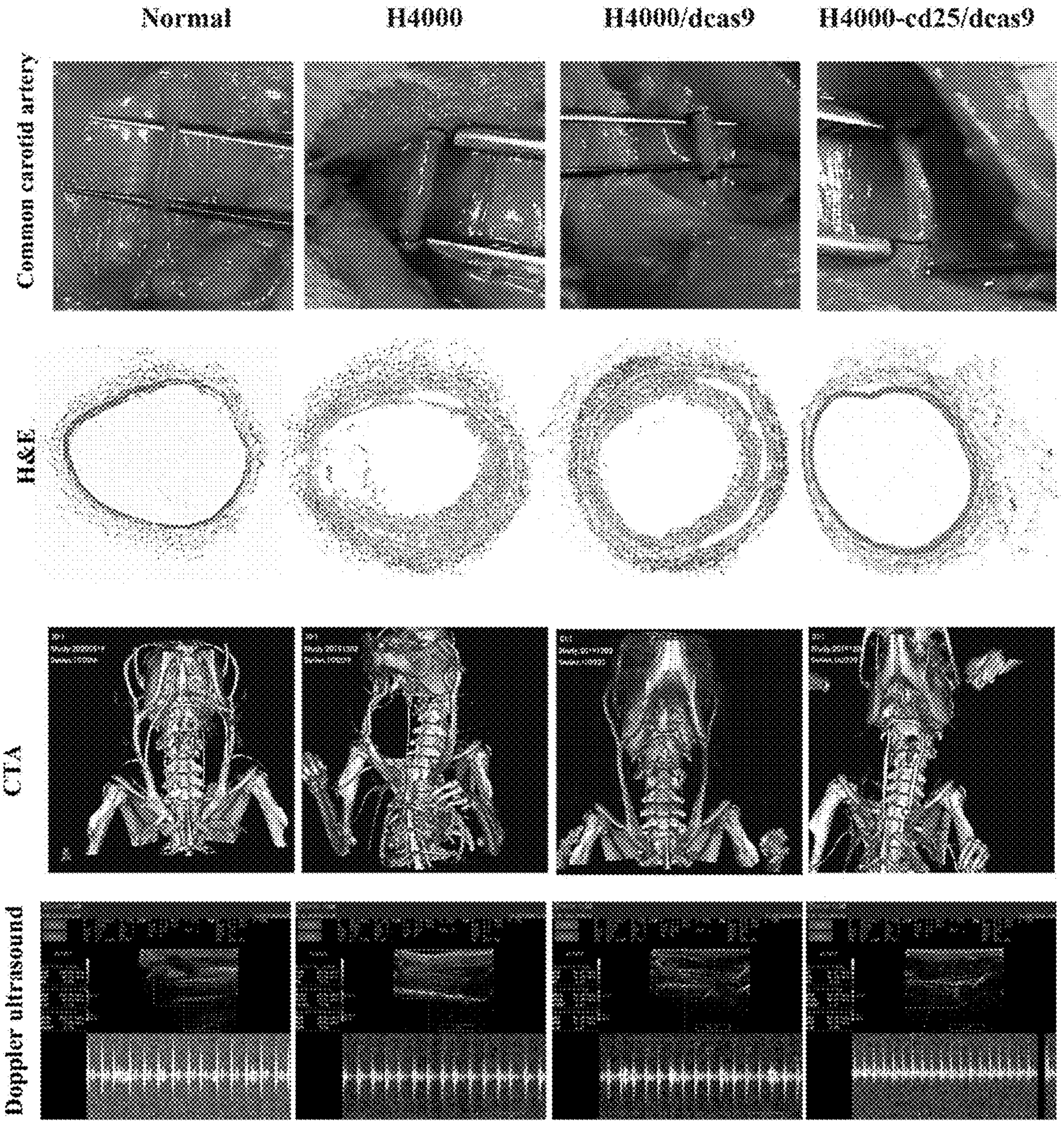
FIG. 10 is a graph showing hematoxylin-eosin (HE) staining to detect vascular morphology and cell aggregation after vascular graft, and small animal computed tomography (CT) and ultrasonography to detect blood flow patency.

(4) Observation of vascular patency: As shown in FIG. 10, the well-constructed functional molecule-modified TEBVs (cardiovascular implants) and the control group were transplanted into the allogeneic or xenogeneic common carotid artery through end-to-end anastomosis, which was performed with surgical sutures under the microscope, 10 cases in each group.

One month after the operation, the blood flows of the TEBV-transplanted common carotid artery and the contralateral healthy common carotid artery were measured by Doppler flowmeter. MicroCT scanning was performed by intravenous injection of iohexol to determine differences in vascular morphology and connectivity. Biological blood vessel prostheses were transplanted into the rat carotid artery. After one month, the bioengineered blood vessel modified with H4000-CD25/dcas9 sustained-release nanoparticles prepared by the present disclosure remained unobstructed, with the average blood flow significantly higher than that of the control group; morphological photography and HE staining of frozen sections showed that no thrombosis and intimal hyperplasia was present in the blood vessels, and thrombosis was obvious in the control group.

Figure 12:
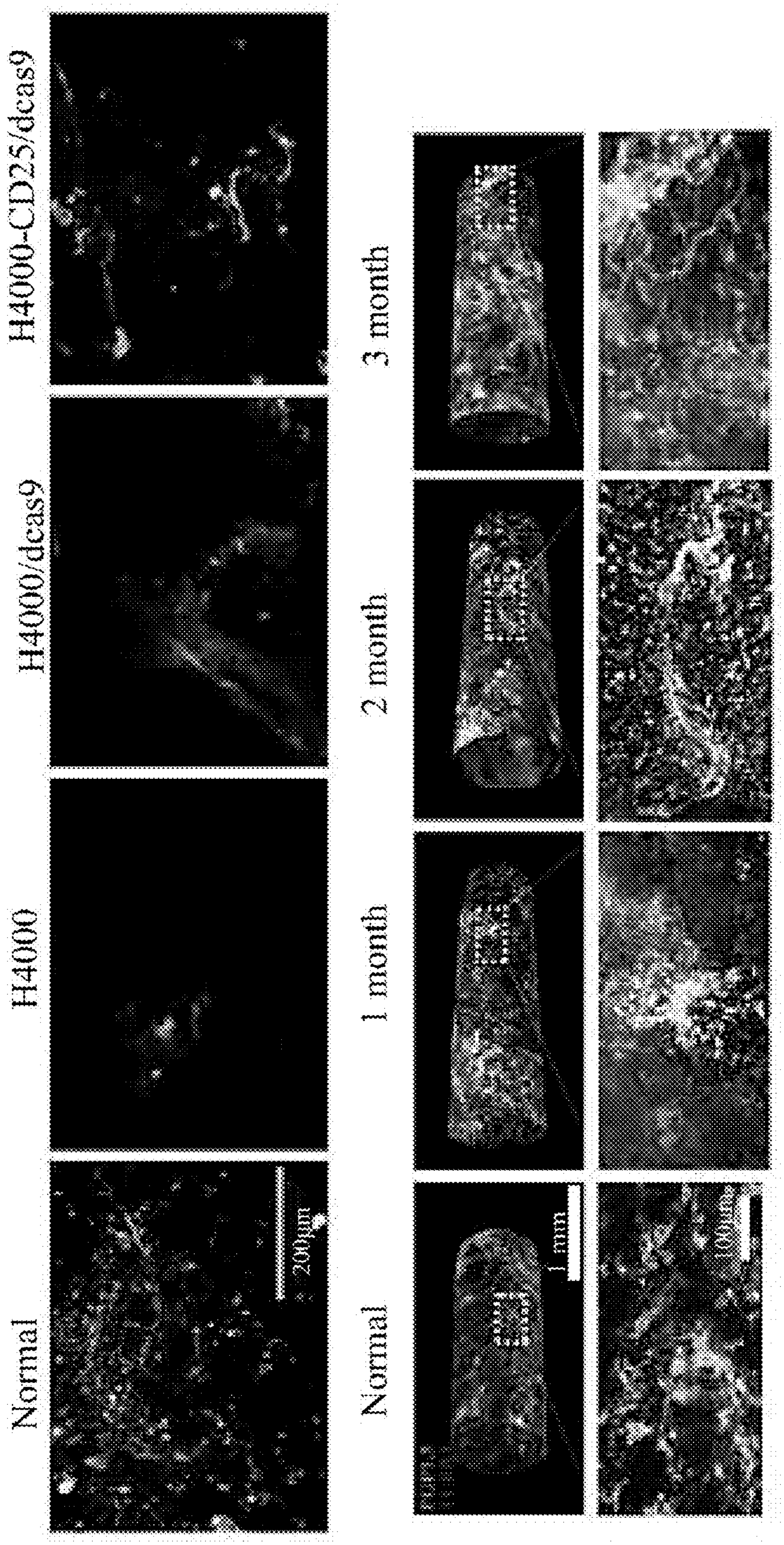
FIG. 12 illustrates the nerve ingrowth and the nerve 3D reconstruction of blood vessels.

(5) Observation of three-dimensional reconstruction of blood vessels and nerves: As shown in FIG. 12, the transplanted H4000-CD25PE/dcas9-transfected engineered blood vessels were taken at 30/60/90 days, respectively. After the clots of the blood vessels were rinsed with normal saline within 2 min, the blood vessels were transferred to 4% formalin to incubate for 3 h and then to 30% sucrose for incubation overnight; adventitias were torn off for stretched preparation, and incubated with PGP9.5 (abcam) and TUBB3 (Bioss) primary antibodies to detect in vivo nerve growth; adventitias were incubated with mouse 488 and rabbit 568 secondary antibodies, and photographs were taken by confocal microscopy; three-dimensional reconstruction of blood vessels and nerves were conducted using 3Dmax software according to the model of blood vessels and nerves, and the in vivo nerve growth was detected and compared.

In the foregoing example of the present disclosure, using the influence and effect of different severity of inflammation on the regeneration of the cardiovascular implant, we constructed a cardiovascular implant modified with H4000-CD25/dcas9 sustained-release nanoparticles, which may induce nerve fiber ingrowth into engineered blood vessels.

The cardiovascular implant modified with H4000-CD25/dcas9 sustained-release nano-system is prepared in the present disclosure. When the cardiovascular implant prepared by the present solution is used for vascular graft, sustained-release nanoparticles may regulate the immune response in-situ, accelerate revascularization, effectively overcome the thrombosis, and promote long-term vascular patency.

The cardiovascular implant constructed by this method can efficiently recognize the aggregated Treg cells, activate and enhance inflammatory inhibition thereof, and realize in-situ regulation of attached macrophages, thereby promoting inflammatory outcome and creating an excellent local microenvironment to accelerate vascular and nerve regeneration; the antithrombotic function of the cardiovascular implant is improved and in-situ regeneration of the cardiovascular implant is accelerated by means of the regulation ability of Treg cells to immune response.

Collagen is a substance commonly used in the field of biomedicine, with high safety and biocompatibility. Given the characteristics of high mechanical strength, strong pressure bearing ability and excellent biocompatibility of collagen nanoparticles, the transfected nanoparticles are encapsulated in the collagen and cross-linked on the surface of the cardiovascular implant body by layer-by-layer self-assembly, achieving sustained release of H4000-CD25/dcas9 nanoparticles and prolonging the expiration date of patency of the cardiovascular implant.

The dcas9 plasmid sequence is shown in SEQ ID NO: 1:

ATGGACAAGAAGTACTCCATTGGCCTCGCCATCGGAACAAATAGCGTGGGCT

GGGCTGTCATCACAGATGAGTACAAGGTGCCTAGCAAGAAATTTAAGGTGCTGGGA

AATACAGACAGACATAGCATCAAGAAGAACCTCATTGGCGCTCTCCTGTTTGACTCC

GGCGAAACAGCCGAAGCTACCAGACTCAAGAGAACCGCTAGGAGAAGGTACACCA

GAAGGAAAAACAGGATTTGCTACCTGCAGGAAATTTTTTCCAACGAGATGGCCAAG

GTGGACGATTCCTTCTTCCATAGGCTGGAAGAGAGCTTCCTCGTGGAGGAAGACAA

GAAACACGAGAGGCATCCTATTTTTGGCAATATTGTGGATGAGGTCGCCTACCATGA

GAAGTATCCCACAATCTATCATCTGAGAAAAAAACTGGTGGATAGCACCGACAAGG

CCGATCTCAGGCTCATTTATCTCGCTCTGGCTCACATGATCAAGTTTAGGGGCCACTT

CCTGATCGAAGGCGACCTGAATCCCGACAACTCCGACGTGGACAAACTGTTCATCC

AGCTCGTCCAGACCTACAATCAACTCTTCGAGGAGAACCCCATCAATGCTTCCGGCG

TGGATGCCAAGGCCATCCTGAGCGCTAGGCTCTCCAAGTCCAGGAGGCTGGAAAAT

CTGATCGCCCAACTCCCTGGAGAGAAGAAGAACGGCCTGTTTGGCAATCTGATTGCC

CTGAGCCTCGGACTCACCCCCAACTTCAAGAGCAACTTCGATCTCGCCGAAGACGCC

AAACTCCAACTGAGCAAGGATACCTACGACGACGATCTCGATAATCTCCTCGCCCA

GATCGGCGATCAATATGCCGACCTCTTTCTGGCCGCCAAAAACCTGAGCGACGCTAT

TCTGCTCAGCGACATTCTCAGGGTGAATACAGAAATCACAA

AAGCCCCCCTGTCCGCCAGCATGATCAAAAGGTACGATGAACACCATCAGGACCTC

ACCCTGCTGAAGGCTCTGGTCAGGCAGCAACTCCCCGAAAAGTACAAGGAGATTTT

CTTTGATCAGTCCAAGAATGGATATGCTGGCTATATTGATGGAGGCGCCTCCCAGGA

GGAATTTTATAAATTCATCAAGCCCATTCTCGAAAAGATGGACGGAACCGAAGAGC

TGCTGGTCAAACTCAATAGGGAGGATCTGCTGAGGAAGCAAAGGACCTTCGACAAT

GGCAGCATCCCCCACCAGATCCACCTCGGCGAACTCCACGCTATCCTCAGGAGGCA

GGAAGACTTCTACCCTTTCCTGAAGGATAACAGGGAGAAAATCGAGAAAATCCTGA

CCTTCAGAATCCCCTACTACGTCGGACCTCTCGCCAGGGGCAATTCCAGATTCGCCT

GGATGACAAGGAAGAGCGAGGAAACAATCACACCATGGAACTTCGAAGAAGTGGT

CGATAAGGGCGCCAGCGCCCAGAGCTTCATTGAAAGGATGACCAACTTTGATAAGA

ACCTGCCCAATGAGAAGGTGCTGCCTAAGCACTCCCTGCTGTATGAGTATTTCACCG

TGTATAATGAGCTGACCAAGGTCAAGTACGTCACCGAGGGAATGAGAAAGCCTGCT

TTTCTCTCCGGCGAGCAGAAAAAAGCCATCGTGGACCTGCTGTTCAAGACCAACAG

GAAGGTGACCGTCAAGCAACTCAAGGAGGACTACTTTAAGAAGATTGAGTGCTTTG

ATAGCGTGGAAATTAGCGGAGTCGAGGACAGGTTCAATGCCTCCCTCGGAACATAT

CACGACCTGCTGAAAATCATCAAAGACAAAGATTTTCTGGATAACGAGGAGAATGA

AGACATTCTGGAGGACATTGTCCTCACCCTGACCCTGTTTGAGGACAGAGAGATGAT

TGAAGAGAGGCTGAAAACCTATGCCCACCTGTTCGACGACAAGGTGATGAAGCAGC

TCAAAAGAAGGAGATATACCGGCTGGGGCAGACTGTCCAGGAAGCTGATCAACGGC

-continued

ATTAGGGACAAGCAGAGCGGCAAGACCATTCTCGACTTTCTCAAGTCCGACGGATT

CGCCAACAGAAACTTTATGCAACTGATCCACGATGACAGCCTCACCTTTAAGGAAG

ATATTCAGAAGGCTCAGGTCAGCGGCCAAGGCGATTCCCTCCATGAGCACATCGCT

AATCTGGCTGGCTCCCCTGCTATCAAAAAGGGCATCCTCCAGACAGTCAAAGTCGTC

GATGAG

CTGGTCAAGGTGATGGGCAGGCATAAACCCGAGAACATTGTGATTGAGATGGCTAG

GGAGAACCAGACCACCCAGAAAGGCCAGAAAAACAGCAGAGAAAGAATGAAGAG

GATCGAGGAGGGCATCAAAGAACTGGGCAGCCAAATCCTCAAGGAGCACCCCGTCG

AAAATACACAACTCCAGAACGAAAAACTCTACCTCTACTATCTGCAGAACGGCAGA

GACATGTACGTGGACCAGGAACTGGACATCAACAGGCTCTCCGATTACGATGTGGA

CGCCATCGTCCCTCAGTCCTTTCTGAAAGATGATAGCATCGACAACAAGGTGCTGAC

CAGGTCCGACAAGAATAGGGGCAAGAGCGATAATGTGCCCTCCGAGGAGGTCGTCA

AAAAAATGAAAAACTACTGGAGACAACTCCTCAACGCTAAGCTCATCACCCAAAGA

AAGTTCGACAATCTGACCAAAGCCGAGAGGGGCGGCCTCTCCGAACTGGACAAGGC

CGGCTTCATCAAAAGGCAATTGGTGGAAACCAGGCAGATTACAAAGCATGTCGCTC

AAATTCTCGATAGCAGGATGAATACCAAATATGACGAGAACGACAAGCTGATCAGA

GAGGTCAAGGTCATCACACTCAAGTCCAAGCTCGTGAGCGACTTCAGAAAAGATTT

CCAATTTTATAAAGTCAGGGAGATCAACAATTACCACCACGCTCACGACGCTTATCT

CAACGCTGTCGTGGGAACCGCCCTGATCAAAAAATACCCCAAGCTGGAAAGCGAGT

TCGTGTATGGCGATTATAAAGTGTACGACGTGAGGAAGATGATCGCTAAAAGCGAG

CAGGAAATCGGCAAGGCTACAGCCAAGTACTTTTTCTACTCCAACATTATGAACTTC

TTCAAGACCGAGATTACCCTCGCCAACGGCGAAATTAGGAAGAGGCCCCTGATTGA

AACAAATGGAGAAACAGGCGAAATCGTCTGGGACAAGGGCAGGGACTTCGCCACA

GTCAGAAAAGTGCTGTCCATGCCTCAAGTCAACATCGTCAAAAAGACCGAGGTGCA

GACCGGCGGCTTTAGCAAAGAAAGCATCCTGCCCAAGAGAAACTCCGACAAGCTCA

TCGCTAGGAAGAAGGACTGGGACCCTAAGAAATACGGAGGATTTGACTCCCCTACC

GTCGCCTATTCCGTCCTCGTCGTCGCTAAGGTGGAGAAGGGCAAGAGCAAGAAGCT

CAAGAGCGTCAAGGAGCTGCTGGGAATCACCATCATGGAGAGGAGCTCCTTCGAAA

AAAACCCTAT

TGATTTCCTGGAGGCCAAGGGCTACAAGGAGGTCAAGAAGGACCTCATCATCAAGC

TGCCCAAATACAGCCTCTTCGAACTGGAAAATGGCAGGAAGAGAATGCTCGCTAGC

GCCGGCGAGCTCCAGAAAGGAAATGAGCTGGCTCTGCCCAGCAAGTACGTCAACTT

CCTCTATCTCGCCAGCCACTATGAAAAGCTCAAGGGCAGCCCCGAAGACAATGAGC

AGAAGCAGCTCTTCGTCGAGCAGCACAAGCACTACCTCGATGAAATCATCGAGCAA

ATCAGCGAGTTTTCCAAAAGGGTGATTCTCGCCGACGCTAACCTCGATAAGGTCCTC

TCCGCTTACAACAAGCATAGAGACAAGCCCATCAGAGAACAGGCCGAGAACATCAT

CCACCTGTTTACACTCACAAACCTCGGAGCCCCTGCCGCTTTTAAATACTTCGATAC

AACCATTGATAGGAAGAGGTACACCTCCACCAAGGAGGTGCTGGATGCTACCCTGA

TTCATCAATCCATCACAGGACTCTACGAAACAAGGATTGACCTGTCCCAACTGGGAG

GCGAC

This specific example is only an explanation of the present disclosure, but it does not limit the present disclosure. Those skilled in the art can make modifications without creative contribution to the present example as needed after reading this specification, but these modifications are protected by the patent law as long as they fall within the scope of the present disclosure.

Sequence Listing Information:
- DTD Version: V1_3
- File Name: GWP20221000218_sequence listing.xml
- Software Name: WIPO Sequence
- Software Version: 2.2.0
- Production Date: 2022 Nov. 9

General Information:
- Current application/Applicant file reference: GWP20221000218
- Earliest priority application/IP Office: CN
- Earliest priority application/Application number: 202111646804.5
- Earliest priority application/Filing date: 2021 Dec. 29
- Applicant name: Army Medical University
- Applicant name/Language: en
- Invention title: CARDIOVASCULAR IMPLANT BASED ON IN-SITU REGULATION OF IMMUNE RESPONSE AND METHOD FOR MAKING THE SAME (en)
- Sequence Total Quantity: 1

Sequences:
- Sequence Number (ID): 1
- Length: 4104
- Molecule Type: DNA
- Features Location/Qualifiers:
  - source, 1 . . . 4104
    - mol_type, other DNA
    - note, DNA sequence of the dcas9 plasmid
    - organism, synthetic construct Residues:

```
atggacaaga agtactccat tggcctcgcc atcggaacaa atagcgtggg ctgggctgtc      60
atcacagatg agtacaaggt gcctagcaag aaatttaagg tgctgggaaa tacagacaga     120
catagcatca agaagaacct cattggcgct ctcctgtttg actccggcga aacagccgaa     180
gctaccagac tcaagagaac cgctaggaga aggtacacca gaaggaaaaa caggatttgc     240
tacctgcagg aaatttttc caacgagatg gccaaggtgg acgattcctt cttccatagg     300
ctggaagaga gcttcctcgt ggaggaagac aagaaacacg agaggcatcc tatttttggc     360
aatattgtgg atgaggtcgc ctaccatgag aagtatccca caatctatca tctgagaaaa     420
aaactggtgg atagcaccga caaggccgat ctcaggctca tttatctcgc tctggctcac     480
atgatcaagt ttaggggcca cttcctgatc gaaggcgacc tgaatcccga caactccgac     540
gtggacaaac tgttcatcca gctcgtccag acctacaatc aactcttcga ggagaacccc     600
atcaatgctt ccggcgtgga tgccaaggcc atcctgagcg ctaggctctc caagtccagg     660
aggctggaaa atctgatcgc ccaactccct ggagagaaga agaacggcct gtttggcaat     720
ctgattgccc tgagcctcgg actcaccccc aacttcaaga gcaacttcga tctcgccgaa     780
gacgccaaac tccaactgag caaggatacc tacgacgacg atctcgataa tctcctcgcc     840
cagatcggcg atcaatatgc cgacctcttt ctggccgcca aaaacctgag cgacgctatt     900
ctgctcagcg acattctcag ggtgaataca gaaatcacaa aagccccct gtccgccagc     960
atgatcaaaa ggtacgatga acaccatcag gacctcaccc tgctgaaggc tctggtcagg    1020
cagcaactcc ccgaaaagta caaggagatt ttctttgatc agtccaagaa tggatatgct    1080
ggctatattg atggaggcgc ctcccaggag gaattttata aattcatcaa gcccattctc    1140
gaaaagatgg acggaaccga agagctgctg gtcaaactca atagggagga tctgctgagg    1200
aagcaaagga ccttcgacaa tggcagcatc ccccaccaga tccacctcgg cgaactccac    1260
gctatcctca ggaggcagga agacttctac cctttcctga aggataacag ggagaaaatc    1320
gagaaaatcc tgaccttcag aatcccctac tacgtcggac ctctcgccag gggcaattcc    1380
agattcgcct ggatgacaag gaagagcgag gaaacaatca caccatggaa cttcgaagaa    1440
gtggtcgata agggcgccag cgcccagagc ttcattgaaa ggatgaccaa ctttgataag    1500
aacctgccca atgagaaggt gctgcctaag cactccctgc tgtatgagta tttcaccgtg    1560
tataatgagc tgaccaaggt caagtacgtc accgagggaa tgagaaagcc tgcttttctc    1620
tccggcgagc agaaaaaagc catcgtggac ctgctgttca agaccaacag gaaggtgacc    1680
gtcaagcaac tcaaggagga ctactttaag aagattgagt gctttgatag cgtggaaatt    1740
```

-continued

```
agcggagtcg aggacaggtt caatgcctcc ctcggaacat atcacgacct gctgaaaatc    1800
atcaaagaca aagattttct ggataacgag gagaatgaag acattctgga ggacattgtc    1860
ctcaccctga ccctgtttga ggacagagag atgattgaag agaggctgaa aacctatgcc    1920
cacctgttcg acgacaaggt gatgaagcag ctcaaaagaa ggagatatac cggctggggc    1980
agactgtcca ggaagctgat caacggcatt agggacaagc agagcggcaa gaccattctc    2040
gactttctca agtccgacgg attcgccaac agaaacttta tgcaactgat ccacgatgac    2100
agcctcacct ttaaggaaga tattcagaag gctcaggtca gcggccaagg cgattccctc    2160
catgagcaca tcgctaatct ggctggctcc cctgctatca aaaagggcat cctccagaca    2220
gtcaaagtcg tcgatgagct ggtcaaggtg atgggcaggc ataaacccga gaacattgtg    2280
attgagatgg ctagggagaa ccagaccacc cagaaaggcc agaaaaacag cagagaaaga    2340
atgaagagga tcgaggaggg catcaaagaa ctgggcagcc aaatcctcaa ggagcacccc    2400
gtcgaaaata cacaactcca gaacgaaaaa ctctacctct actatctgca gaacggcaga    2460
gacatgtacg tggaccagga actggacatc aacaggctct ccgattacga tgtggacgcc    2520
atcgtccctc agtcctttct gaaagatgat agcatcgaca acaaggtgct gaccaggtcc    2580
gacaagaata ggggcaagag cgataatgtg ccctccgagg aggtcgtcaa aaaaatgaaa    2640
aactactgga gacaactcct caacgctaag ctcatcaccc aaagaaagtt cgacaatctg    2700
accaaagccg agaggggcgg cctctccgaa ctggacaagg ccggcttcat caaaaggcaa    2760
ttggtggaaa ccaggcagat tacaaagcat gtcgctcaaa ttctcgatag caggatgaat    2820
accaaatatg acgagaacga caagctgatc agagaggtca aggtcatcac actcaagtcc    2880
aagctcgtga gcgacttcag aaaagatttc caattttata aagtcaggga gatcaacaat    2940
taccaccacg ctcacgacgc ttatctcaac gctgtcgtgg gaaccgccct gatcaaaaaa    3000
taccccaagc tggaaagcga gttcgtgtat ggcgattata aagtgtacga cgtgaggaag    3060
atgatcgcta aaagcgagca ggaaatcggc aaggctacag ccaagtactt tttctactcc    3120
aacattatga acttcttcaa gaccgagatt accctcgcca acggcgaaat taggaagagg    3180
cccctgattg aaacaaatgg agaaacaggc gaaatcgtct gggacaaggg cagggacttc    3240
gccacagtca gaaaagtgct gtccatgcct caagtcaaca tcgtcaaaaa gaccgaggtg    3300
cagaccggcg gctttagcaa agaaagcatc ctgcccaaga gaaactccga caagctcatc    3360
gctaggaaga aggactggga ccctaagaaa tacggaggat ttgactcccc taccgtcgcc    3420
tattccgtcc tcgtcgtcgc taaggtggag aagggcaaga gcaagaagct caagagcgtc    3480
aaggagctgc tgggaatcac catcatggag aggagctcct tcgaaaaaaa ccctattgat    3540
ttcctggagg ccaagggcta caaggaggtc aagaaggacc tcatcatcaa gctgcccaaa    3600
tacagcctct tcgaactgga aaatggcagg aagagaatgc tcgctagcgc cggcgagctc    3660
cagaaaggaa atgagctggc tctgcccagc aagtacgtca acttcctcta tctcgccagc    3720
cactatgaaa agctcaaggg cagccccgaa gacaatgagc agaagcagct cttcgtcgag    3780
cagcacaagc actacctcga tgaaatcatc gagcaaatca gcgagttttc caaaagggtg    3840
attctcgccg acgctaacct cgataaggtc ctctccgctt acaacaagca tagagacaag    3900
cccatcagag aacaggccga gaacatcatc cacctgttta cactcacaaa cctcggagcc    3960
cctgccgctt ttaaatactt cgatacaacc attgatagga agaggtacac ctccaccaag    4020
gaggtgctgg atgctaccct gattcatcaa tccatcacag gactctacga aacaaggatt    4080
gacctgtccc aactgggagg cgac                                            4104
```

END

What is claimed is:

1. A cardiovascular implant based on in-situ regulation of immune response, comprising a cardiovascular implant body and H4000-CD25/dSpcas9 sustained-release nanoparticles modified on the cardiovascular implant body; wherein the H4000-CD25/dSpcas9 sustained-release nanoparticles comprise an H4000 plasmid nanocarrier, an anti-CD25 antibody, and a dSpcas9 system plasmid comprising (i) a nucleotide sequence encoding dSpCas9-NLS-VP64 protein, and (ii) a nucleotide sequence encoding a single guide RNA comprising a sequence selected from the group consisting of SEQ ID NO: 2, 3, and 4; wherein the H4000 plasmid nanocarrier and the anti-CD25 antibody are covalently linked, and wherein the dSpcas9 system plasmid sequence is capable of enhancing expression of TET2.

2. The cardiovascular implant based on in-situ regulation of immune response according to claim 1, wherein the cardiovascular implant is tubular, 1-4 mm in diameter, and 0.5-20 cm in length.

3. A method for preparing the cardiovascular implant based on in-situ regulation of immune response according to claim 1, comprising the following steps:

step 1, constructing a cardiovascular implant body;

step 2, preparing an H4000-CD25 nanotransfection vector, wherein the nanotransfection vector comprises an H4000 plasmid nanocarrier and an anti-CD25 antibody, and wherein the H4000 plasmid nanocarrier and the anti-CD25 antibody are covalently linked;

step 3, preparing H4000-CD25/dSpcas9 sustained-release nanoparticles by combining the H4000-CD25 nanotransfection vector and a dSpcas9 system-plasmid, wherein the dSpcas9 plasmid comprises (i) a nucleotide sequence encoding dSpCas9-NLS-VP64 protein, and (ii) a nucleotide sequence encoding a single guide RNA comprising a sequence selected from the group consisting of SEQ ID NO: 2, 3 and 4; and step 4, conjugating the H4000-CD25/dSpcas9 sustained-release nanoparticles on the cardiovascular implant body: co-incubating the cardiovascular implant body with the H4000-CD25/dSpcas9 sustained-release nanoparticles and collagen to obtain the cardiovascular implant.

4. The method according to claim 3, wherein a method for constructing the cardiovascular implant body in step 1 comprises: removing cells and then nucleic acids and fats from isolated blood vessels to obtain a blood vessel matrix material; and covering collagen on a surface of the blood vessel matrix material to obtain the cardiovascular implant body.

5. The method according to claim 3, wherein the H4000-CD25/dSpcas9 sustained-release nanoparticles in step 3 are prepared by encapsulating the Crispr/dSpcas9 system plasmid in the H4000-CD25 nanotransfection vector, and wherein the Crispr/dSpcas9 plasmid is incubated with the H4000-CD25 nanotransfection vector at 0.4 μg of plasmid/μL of transfection vector.

6. The method according to claim 3, wherein conjugating the H4000-CD25/dSpcas9 sustained-release nanoparticles on the cardiovascular implant body in step 4 comprises: conducting a first incubation of the cardiovascular implant body with the H4000-CD25/dSpcas9 sustained-release nanoparticles for 10 min, and conducting a second incubation of the cardiovascular implant body with the collagen for 10 min; and repeating the first and second incubations twice to obtain a self-assembled cardiovascular implant modified with the H4000-CD25/dSpcas9 sustained-release nanoparticles.

* * * * *